April 25, 1972 D. L. ARMSTRONG Plant Pat. 3,131
ROSE PLANT
Filed May 27, 1970
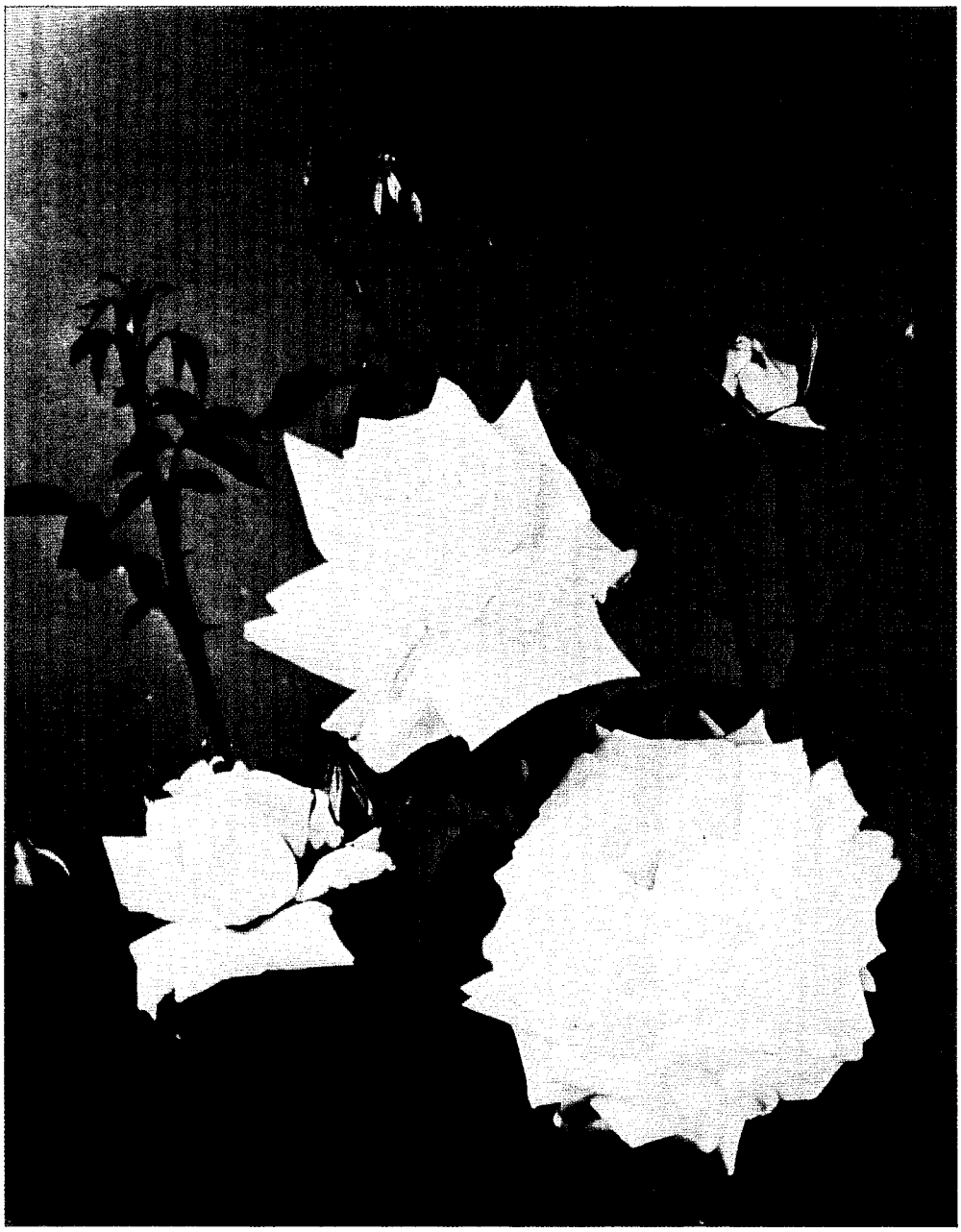

United States Patent Office

Plant Pat. 3,131

Patented Apr. 25, 1972

3,131

ROSE PLANT

David L. Armstrong, Upland, Calif., assignor to Armstrong Nurseries, Inc., Ontario, Calif.

Filed May 27, 1970, Ser. No. 41,120
Int. Cl. A01h 5/00
U.S. Cl. Plt.—11 1 Claim

ABSTRACT OF THE DISCLOSURE

An upright, vigorous many-branched rose plant of the hybrid tea class, having a scarcity of large prickles on its main stems, and slightly above average resistance to mildew. Plant blooms grow on single, long strong stems, and are of large size. Petalage is very double, the petals being thick and slightly shiny. Overall color effect is white, with pink-tinted apices on certain of the reflexed petals and in the heart of the bloom.

This invention relates to a hybrid tea rose grown as an outdoor seedling for cut flowers and garden decoration. It it a tall bush. Its hardiness in diverse climactic conditions has not yet been tested. It was grown in Ontario, Calif.

The plant is a seedling having as its seed parent Garden Party, and as its pollen parent Sweet Afton. It holds its distinguishing characteristics through succeeding propagations by budding.

The accompanying drawing illustrates the plant in color and shows the flowering thereof from bud to full bloom.

This new variety may be distinguished from its seed parent, Garden Party, in the following characteristics:

The new variety has a bloom which is very double, with from 30–37 petals, plus petaloids. Although Garden Party has a double flower, it has fewer petals, ranging from 25–30.

The fragrance of the new variety is quite strong, a blend of tea rose and spice. By comparison, the fragrance of Garden Party is relatively slight.

The color of this new variety is nearly white, slightly tinged with pale purplish pink, whereas the blooms of Garden Party range from pale yellow to white, slightly tinged with a light pink on the margins of the petals. The new variety displays a pink coloration on the outer surfaces of the petals, whereas the pink coloration in Garden Party is substantially more pronounced in intensity and appears primarily on the interior surfaces of the petals.

The petals of this new variety are more slender and more flat than the petals of Garden Party, which are extremely large and cup-shaped. The bud of this new variety is ovoid in shape, whereas Garden Party has an urn-shaped bud.

The plant of this new variety is taller and more upright than Garden Party.

This new variety has substantially greater resistance to mildew, as compared to Garden Party under comparable conditions.

This new variety is distinguished from its pollen parent, Sweet Afton, in the following characteristics:

This new variety has an ovoid bud which is relatively short, as compared to Sweet Afton, which has an extremely long and urn-shaped bud.

This new variety, though upright, free and vigorous, is substantially less vigorous and less tall than the pollen parent, Sweet Afton.

The new variety has very few prickles on the main stems, and they are of medium length and almost straight, The prickles on the main stems of Sweet Afton, by contrast, are more numerous and range from medium-length to long and are hooked slightly downward.

The petals of this new variety are fairly narrow, whereas the petals of Sweet Afton are extremely broad.

Although the basic color of both of these varieties is near white, the petals of Sweet Afton are definitely shaded a blush pink, whereas the color of this new variety is only slightly tinged with pink and usually only on the tips of the petals.

The leaflets of this new variety are ovoid and relatively narrow in relation to their length. The leaflets of Sweet Afton are broadly oval.

The flowers are usually borne singly on strong long stems. Sometimes three will be carried in an irregular cluster on a single stem. The plant blooms freely outdoors, and almost continuously during the growing season. The fragrance is strong to spicy, reminiscent of tea and rose.

Color means beginning with a small letter signify that the name of that color, as used in common speech, is aptly descriptive. Color names beginning with a capital letter designate values based upon the Nickerson Color Fan, put out by Munsell Color Co., throughout this case.

*Bud*

The peduncle is of average length, heavy and stiff. It is usually smooth and its color is Moderate Yellow Green, 5 GY 5/6, overlaid with intermittent speckles of Dark Red, 5 R 3/7, on the side exposed to the sun.

Before the calyx breaks, the bud is of medium size and medium length. It is ovoid in form, with foliaceous appendages, and a few gland-tipped cilia on the surface of the bud. Usually, there are slender foliaceous parts extending beyond the tip of the bud for a distance equal to about ¼ or more of its length.

As the calyx breaks, the color is nearly Brilliant Yellow Green, 2.5 GY 9/8, for the lower half of the petal, lightening towards white at the petal apex, with an overlay of Strong Purplish Pink, 7.5 RP 5/12.

The inner surface of the sepals is covered with a fine tomentum. Margins of alternate sepals are lined with a fine wooly tomentum, the margins of the other sepals being lined with stipitate glands and occasional slender foliaceous appendages.

As the first petal opens, the size is large and the form is ovoid. On the outer surface there are veins at a small portion of the base which are Strong Yellow Green, 5 GY 6/8, with an area of Brilliant Yellow Green, 2.5 GY 9/8, changing gradually to nearly white and into a slight tipping of the petals with Light Purplish Pink, 7.5 RP 8/5. Inside there is a small area at the base of the petal which is Strong Greenish Yellow, 10 Y 8/11, lightening to a near white on most of the petals. The upper edges have an overlay of near Pale Purplish Pink, 7.5 RP 9/2.

The bud opens up well. It is not retarded or prevented from opening by cold, hot, wet, or dry weather.

*Bloom*

When fully open, the blooms are of large size, being 4″–5″ across. The petalage is very double, ranging from 30–37 petals, plus 6–8 petaloids, which are regularly arranged.

The form of the bloom is high-centered at first, becoming open to high-centered. The petals at first are loosely cupped with tips rolled outwards, becoming at maturity more flat, with tips reflexed. The petals are thick, of a moderately leathery texture, the inside being slightly shiny to velvety, the outside slightly shiny.

The shape of the outside petal is obovate, and scalloped, usually with one to three notches. The intermediate petals are obovate, with apex rounded, and the inside petals are nearly round. They are scalloped, the apex also being rounded, and have from one to three notches.

The following description applies to a newly opened flower in the month of April, in Ontario, Calif. The plant was grown outdoors.

The outer surface of the outside petal is near white with an overlay of Brilliant Yellow Green, 2.5 GY 9/8, through a moderate area at the base and with small areas of Moderate Purplish Red, 5 RP 4/10, at the apex and fringing the petal. The inner surface of the outside petal is near white, with a small area near the base overlaid with near Brilliant Greenish Yellow, 7.5 Y 9/8, having a fringe and apex overlaid with Light Purplish Pink, 7.5 RP 8/5.

The outer surface of the intermediate petal is near white, with an overlay of Brilliant Yellow Green, 2.5 GY 9/8, in a small area at the base and with very slight overlay of Pale Purplish Pink, 7.5 RP 9/2, fringing the apex. The inner surface of the intermediate petal is nearly white with a small area at the base near Brilliant Greenish Yellow, 10 Y 9/9, and with very slight overlay of Pale Purplish Pink, 7.5 RP 9/2 fringing the apex.

The outer surface of the inner petal is nearly white with a small area at the base overlaid with Strong Greenish Yellow, 10 Y 8/11, which lightens as it progresses halfway up the petal. The apex is overlaid with Pale Purplish Pink, 7.5 RP 9/2. The inner surface of the inside petal is nearly white with a small area at the base a Vivid Greenish Yellow, 7.5 Y 8/12, lightening rapidly for a moderate area of the base and with very slight overlay of Pale Purplish Pink, 7.5 RP 9/2 at apex.

The description which follows was made from a rose that had been open for three days during the month of April. It was taken from a plant grown outdoors in Ontario, Calif.

The outer surface of the outside petal is nearly white with a slight overlay of Pale Purplish Pink, 7.5 RP 9/2, towards the apex. The inner surface of the outside petal is nearly white with a slight overlay of Brilliant Greenish Yellow, 10 Y 9/9, in a small area at the base.

The outer surface of the inside petal is nearly white with a very slight overlay of Brilliant Yellow Green, 2.5 GY 9/8, at a small area of the base, and a faint overlay of Pale Purplish Pink, 7.5 RP 9/2, towards the apex. The inner surface of the inside petal is nearly white with a small area at the base of a Brilliant Greenish Yellow, 10 Y 9/9.

The general color effect of the newly opened flower is nearly white with overlay of a coloration which lies between Pale Purplish Pink, 7.5 RP 9/2, and Light Purplish Pink, 7.5 RP 8/5, on the apex of the petals, with darkened tones near the center of the flower. After the bloom has been three days open, the color effect is nearly white, with a slight overlay of Pale Purplish Pink, 7.5 RP 9/2, on the apex of the intermediate and inner petals.

The petals drop off cleanly, and are not affected by cold, hot, wet, or dry weather.

The flower persists on the bush in the garden for from four to five days in the month of September. Roses grown outdoors, but cut and kept at living-room temperatures, likewise persist for from four to five days in the month of September.

*Reproductive organs*

Stamens: The stamens are of average number, arranged irregularly about the pistils.

Filaments: The filaments are short to long, from 3–10 mms. in length.

Anthers: The anthers are large. They open at various times. On the upper side their color is near Moderate Orange Yellow, 10 YR 8/10; on the under side their color is near Brilliant Yellow, 2.5 Y 9/9.

Pollen: The pollen is somewhat sparse, and is near Strong Orange Yellow, 10 YR 7/10, in color.

Pistils: The pistils are very numerous, approximately about 120.

Styles: The styles are moderatively even, short to average length, thin and somewhat bunched. They are 2–6 mms. in length.

Stigma: The stigma is near Moderate Red, 2.5 R 4/10, in color.

Ovaries: The ovaies are, for the most part, enclosed in the calyx, although some protrude.

Hips: The hips are globular. Their color is near Dark Greenish Yellow, 10 Y 6/7, when they are fully developed but not yet ripe. They are moderately smooth with thick fleshy walls.

Sepals: The sepals fall soon. They are of medium length, and spear-shaped, and their color is not notable.

Seeds: The seeds are about average in number, usually of medium size to large. There may be 14–21 of them.

*Foliage*

The compound leaves comprise 3–5 leaflets and are moderately abundant. They are large and heavy, but also somewhat leathery and semi-glossy in texture. The leaflets are avoid or obovate in shape, with the apex acute, the base obtuse, and the margin simply serrate. The color of the mature foliage on the upper surface is between Moderate Olive Green, 5 GY 4/3, and Grayish Olive Green, 5 GY 3/2. On the under surface, the coloration is Moderate Olive Green, 2.5 GY 4/3, and lighter shading within the veins.

The young growth, on its upper surface, is a color near Moderate Olive Green, 10 Y 4/3, with veining and edges near Dark Red, 2.5 R 3/7. The under surface of the new growth is between Strong Yellow Green, 5 GY 6/8, and Moderate Yellow Green, 5 GY 5/6, with strong overlay of Dark Red, 2.5 R 3/7.

The rachis is of average size, its upper side being grooved and carrying a few stipitate glands on the edges. The under side is moderately smooth, and with stipitate glands.

The stripules are moderately short, of medium width, and with short points, turning out at an angle of more than 90°.

The plant displays a resistance to mildew which is greater than average, when compared to other varieties now grown in commerce under comparable conditions in Ontario, Calif.

*Growth*

The plant is upright and much branched in habit, and vigorous in growth. The canes are of medium caliper.

The main stems are colored near Moderate Yellow Green, 5 GY 5/6. The large prickles which they carry are very few in number, of medium length, and almost straight, with medium-length narrow base. Their color is near Light Olive, 10 Y 5/5. There are no small prickles and no hairs.

The branches have a color near Moderate Yellow Green, 5 GY 5/6. They carry large prickles which are few in number, of medium length, and almost straight, with medium-length narrow bases. Their color is near Strong Yellow Green, 2.5 GY 6/8. They have no small prickles and no hairs.

New shoots have a color which is near Moderate Yellow Green, 2.5 GY 5/5, overlaid with shades of Dark Red, 2.5 R 3/7, where the stem is exposed to direct sunlight. The large prickles which they carry are very few in number, of medium length, almost straight, with medium-length narrow bases. Their color is near Dark Greenish Yellow, 7.5 Y 6/7, overlaid with near Moderate Red, 2.5 R 4/10. There are no small prickles and no hairs on the new shoots.

I claim:

1. A rose plant of the hybrid tea class substantially as shown and described herein, said plant being distignuished by combinations of the following characteristics, namely: its upright, much branched, free and vigorous habit of growth; the fewness of the large prickles on the main stems, these being generally of medium length and straight; the tendency to bear most of its blooms singly on long, strong stems; the relatively large size of the bloom, its very double petalage, its almost white overall color effect, with many petals lightly fringed with pink at their apieces; the strong fragrance, a blending of tea and spice aroma; and a slightly better-than-average resistance to mildew.

No references cited.

ROBERT E. BAGWILL, Primary Examiner

UNITED STATES PATENT OFFICE
CERTIFICATE OF CORRECTION

Patent No. PP 3131 Dated April 25, 1972

Inventor(s) David L. Armstrong

It is certified that error appears in the above-identified patent and that said Letters Patent are hereby corrected as shown below:

Column 1, line 24 - "it" should be --is--

Column 2, line 17 - "means" should be --names--

Column 4, line 26 - "avoid" should be --ovoid--

Column 6, line 1 - "apieces" should be --apices--

Signed and sealed this 19th day of September 1972.

(SEAL)
Attest:

EDWARD M.FLETCHER,JR.
Attesting Officer

ROBERT GOTTSCHALK
Commissioner of Patents

USCOMM-DC 60376-P69
☆ U.S. GOVERNMENT PRINTING OFFICE : 1969 O—366-334